(12) United States Patent
Repka et al.

(10) Patent No.: US 10,583,233 B2
(45) Date of Patent: Mar. 10, 2020

(54) MECHANISM FOR ADJUSTING OCCLUSION OF A CARDIAC BYPASS ROLLER PUMP, AND A ROLLER PUMP PROVIDED WITH THE MECHANISM

(71) Applicant: Maquet Cardiopulmonary GmbH, Rastatt (DE)

(72) Inventors: William James Repka, Parsippany, NJ (US); Daniel A. Walters, Rockaway Township, NJ (US)

(73) Assignee: MAQUET CARDIOPULMONARY GmbH, Rastatt (DE)

( * ) Notice: Subject to any disclaimer, the term of this patent is extended or adjusted under 35 U.S.C. 154(b) by 277 days.

(21) Appl. No.: 15/571,010

(22) PCT Filed: May 12, 2016

(86) PCT No.: PCT/EP2016/060784
§ 371 (c)(1),
(2) Date: Oct. 31, 2017

(87) PCT Pub. No.: WO2016/180951
PCT Pub. Date: Nov. 17, 2016

(65) Prior Publication Data
US 2018/0161486 A1 Jun. 14, 2018

Related U.S. Application Data

(60) Provisional application No. 62/160,741, filed on May 13, 2015.

(51) Int. Cl.
*A61M 1/10* (2006.01)
*F04B 43/12* (2006.01)

(52) U.S. Cl.
CPC ........ *A61M 1/1039* (2014.02); *A61M 1/1006* (2014.02); *F04B 43/1276* (2013.01); *A61M 1/1086* (2013.01); *F04B 43/1253* (2013.01)

(58) Field of Classification Search
CPC .. A61M 1/006; A61M 1/1039; A61M 1/1086; F04B 43/1253; F04B 43/1276
See application file for complete search history.

(56) References Cited

U.S. PATENT DOCUMENTS 487,136 A * 11/1892 Truax ................. F04B 43/1253
                                                  417/477.8
4,043,712 A    8/1977 Azzolini
(Continued)

FOREIGN PATENT DOCUMENTS

CN    101622453 A    1/2010
CN    101784795 A    7/2010
(Continued)

OTHER PUBLICATIONS

"Circuitry and Cannulation Techniques"—Chapter 5 of "Cardiopulmonary Bypass and Mechanical Support"—3rd Edition—Chapter 5 written by Eugene A. Hessel—Textbook edited by Glenn P. Gravlee—pp. 63-65—ISBN/ISSN: 9781451193619.
(Continued)

*Primary Examiner* — Patrick Hamo
*Assistant Examiner* — Joseph S. Herrmann
(74) *Attorney, Agent, or Firm* — Wesley Scott Ashton (57) ABSTRACT

A mechanism for adjusting occlusion of a roller pump is described, wherein the mechanism is provided with: an elongated rod member oriented on a central axis of a pump head of the roller pump; and a drive member attached to the elongated rod member so as to move along the elongated rod member between a first position and a second position, wherein the drive member is connected to each roller block of a pump rotor of the pump head so that movement of the drive member by constant increments along the elongated rod member causes non-uniform and/or non-linear incre- (Continued)

mental movement of each roller block in a direction radial to the central axis of the pump head.

22 Claims, 8 Drawing Sheets

(56) References Cited

U.S. PATENT DOCUMENTS

| | | | | |
|---|---|---|---|---|
| 4,174,193 | A | * | 11/1979 | Sakakibara ......... F04B 43/1253 417/477.8 |
| 4,548,553 | A | * | 10/1985 | Ferster ................ F04B 43/1276 417/477.7 |
| 5,009,573 | A | * | 4/1991 | Ring, Sr. ............. F04B 43/1276 417/475 |
| 5,110,270 | A | | 5/1992 | Morrick |
| 5,657,000 | A | * | 8/1997 | Ellingboe ........... F04B 43/1276 128/DIG. 12 |
| 6,736,617 | B2 | * | 5/2004 | Domroese .......... F04B 43/1253 417/477.3 |
| 6,749,410 | B1 | | 6/2004 | Burch |
| 9,422,932 | B2 | * | 8/2016 | Petersen ............. F04B 43/1276 |
| 2009/0269228 | A1 | | 10/2009 | McIntosh |
| 2012/0175292 | A1 | | 7/2012 | Beiriger |
| 2014/0127063 | A1 | | 5/2014 | Petersen et al. |

FOREIGN PATENT DOCUMENTS

| | | |
|---|---|---|
| DE | 1807979 A1 | 7/1969 |
| WO | 02/066833 A1 | 8/2002 |
| WO | 2014/053858 A1 | 4/2014 |

OTHER PUBLICATIONS

International Search Report and Written Opinion of PCT Application No. PCT/EP2016/060784, dated Aug. 2, 2016, which corresponds to this present application.

Office Action issued in CN Application No. 201680027365.0, dated Nov. 5, 2019.

Office Action Search Report issued in CN Application No. 201680027365.0, dated Oct. 25, 2019.

* cited by examiner

MECHANISM FOR ADJUSTING OCCLUSION OF A CARDIAC BYPASS ROLLER PUMP, AND A ROLLER PUMP PROVIDED WITH THE MECHANISM

This application is a national stage entry (under 35 USC 371) of PCT/EP/2016060784, filed May 12, 2016, which claims the benefit of priority to U.S. Provisional Patent Application 62/160,741, filed May 13, 2015, the disclosure of which are hereby incorporated by reference in their entirety.

FIELD OF THE DISCLOSURE

The present disclosure pertains broadly to the field of roller pumps used in medical devices such as heart-lung machines, ECMO machines, other cardiopulmonary bypass machines, and extracorporeal circulation machines employed for dialysis. More specifically, the field of this disclosure may be construed as directed to an occlusion mechanism, for use in medical devices such as roller pumps for heart-dung machines, ECMO machines, other cardiopulmonary bypass machines, and extracorporeal circulation machines employed for dialysis.

BACKGROUND OF THE DISCLOSURE

Roller pumps, also known as peristaltic pumps, are used in medicine and surgery to circulate blood in extracorporeal circulation machines, such as dialysis machines, and in cardiopulmonary bypass machines, such as heart-lung machines and extracorporeal membrane oxygenation (ECMO) machines. Roller pumps operate to pump fluid, such as blood, by positive displacement using revolving rollers that occlude flexible tubing. With respect to cardiopulmonary bypass machines, multiple roller pumps may be employed as pan of a perfusion circuit to provide aortic root suction, vent suction, a blood cardioplegia pump, and a systemic blood pump. See, e.g., FIG. 1 of Chapter 5, Glenn P. Gravlee et al. (eds), Cardiopulmonary Bypass: Principles and Practices (2008). However, roller pumps may be employed in other environments, such as with a dialyzer or as a pump to feed intravenous (IV) fluids intravenously to a patient.

Roller pumps are simply structured devices that produce a constant flow, and use disposable tubing as a fluid path through which fluid is pumped. Roller pumps generally include a pump drive and a pump head, wherein the pump drive is connected to drive rotation of the pump head to pump fluid. The pump head includes a pump stator and a pump rotor, wherein the pump stator forms a housing that defines an inner circumferential surface, or raceway, against which one or more tubes through which fluid flows are compressed by rollers connected to the pump rotor. Upon rotation of the pump rotor by rotation of a drive shaft connected to the pump rotor, the rollers connected to the pump rotor compress the fluid tubing against the inner circumference of the pump stator so that rolling of the rollers along the tubing pushes fluid in the tubing in the direction of the pump rotor's rotation. The amount of compression (i.e., occlusion) applied by the pump rollers against the fluid tubing needs to be adjusted to compensate for subtle manufacturing differences of fluid tubing with respect to diameter, for example, provided by different vendors, or to compensate for the use of different sized fluid tubing.

Because the fluid flowing in the tubing may include blood, it is important that the roller pumps be adjustable with respect to the degree of compression of the tubing during roller rotation and pumping. If compression is complete so that the walls of the tubing completely collapse during compression, then red blood cells of the pumped blood may be lysed, thereby rendering the pumped blood less suitable for use. If the compression is inadequate so that the walls of the tubing are not adequately compressed during pump rotor rotation, then inadequate fluid flow or even backflow may result. Therefore, it is necessary to be able to adjust the amount of compression the rollers and the raceway exert on the tubing during pump rotor rotation in view of the fact that fluid tubing of different diameters may be used in the roller pumps.

The ability to adjust the amount of compression exerted by the rollers against the fluid tubing in the raceway is known in the art as "occlusion," and this term reflects the degree to which the fluid tubing is compressed, or occluded, between the rollers and the raceway surface during rotation of the pump rotor. Roller pumps are generally provided with a mechanism to adjust occlusion by rotating a knob, or turning some other assembly, in one direction in order to move the rollers radially outward and closer to the inner surface of the pump stator, thereby increasing occlusion, and to rotate the knob, or other assembly, in another direction in order to move the rollers radially inward and away from the inner surface of the pump stator, thereby decreasing occlusion. Thus, when the pump rollers are completely disengaged from the fluid tubing in the raceway, there is a need to be able to rapidly move the pump rollers to engage the fluid tubing in the raceway. When the pump rollers have engaged the fluid tubing in the raceway, there is a need to move the rollers in fine increments in order to finely tune the degree of occlusion. Once the degree of occlusion has been fine-tuned, then the increments are locked into portion for the duration of a pumping procedure. Pump roller increments may be evaluated as the gap distance between the roller and corresponding pans of the fluid tubing path. In addition, all of the rollers of the roller pump are required to maintain the same amount of compression of the fluid tubing.

Significant force is required to compress the fluid tubing to achieve the desired amount of occlusion. The force required by the user to obtain the desired amount of fluid tubing compression is typically directly related to the tube compression force. Prior art actuating mechanisms, such as a thumb wheel actuating mechanisms for instance, for an occlusion adjustment mechanism for a roller pump have poor mechanical advantage. This is undesirable.

Other disadvantages shared by conventional mechanisms for adjusting occlusion of a roller pump are related to the linear nature of the adjustment mechanism. Each turn of the knob, or other adjustment mechanism such as a thumbwheel, produces the same incremental movement of the rollers with respect to the inner surface of the pump stator regardless of whether the rollers are close to the pump stator surface or are located further away from the pump stator surface. In other words, incremental travel of the rollers is, traditionally, linearly proportional to the degree of input motion. This means that for every fractional adjustment made by the user to an actuator, such as a knob, a directly proportional translation of the rollers occurs in a radial direction with respect to the central axis of the rollers. This direct proportionality may be expressed as a ratio of input movement to output movement, such as illustrated by curve A of FIG. 1.

Figure 1:
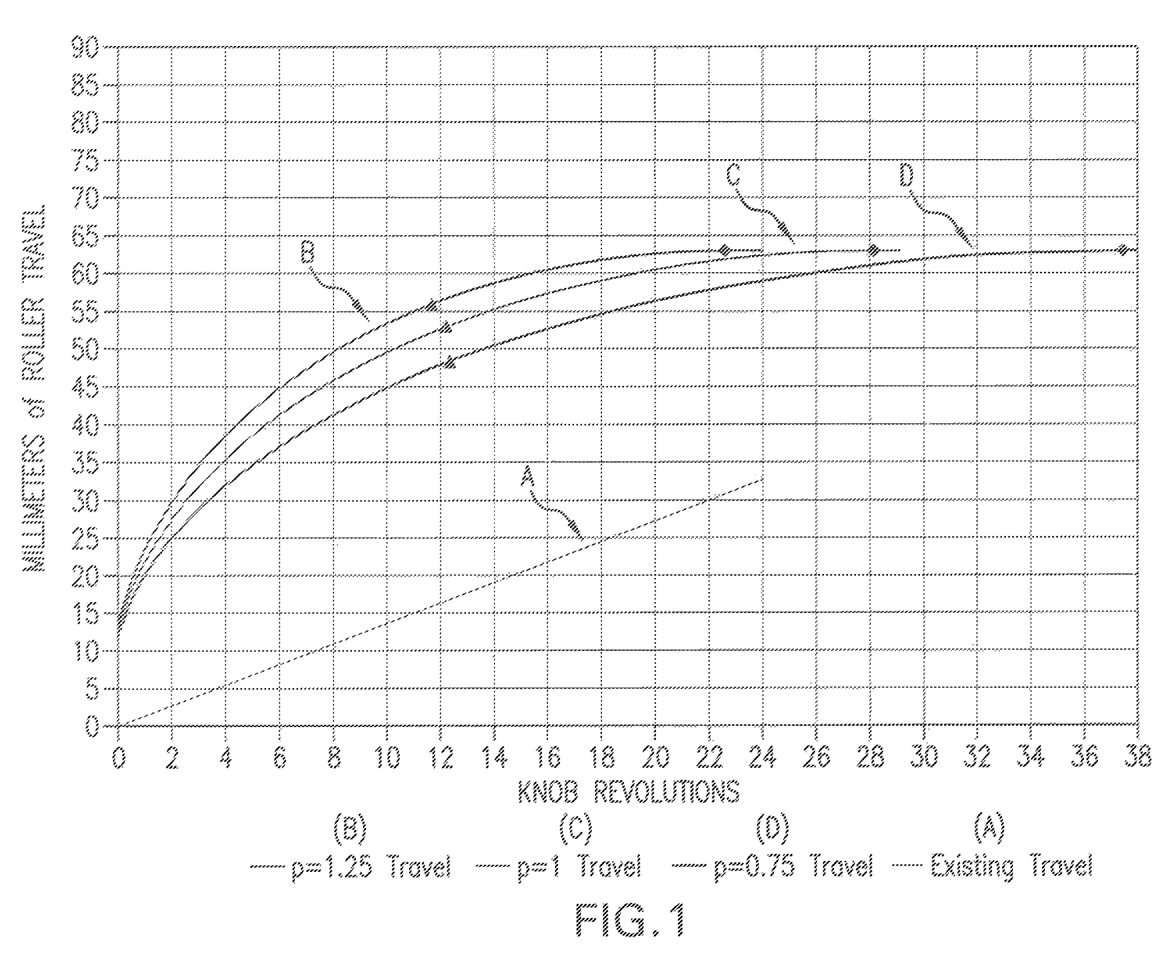
FIG. 1 is a graph of roller displacement versus knob revolutions pertaining to different occlusion adjustment mechanisms for a roller pump.
Figure 2:
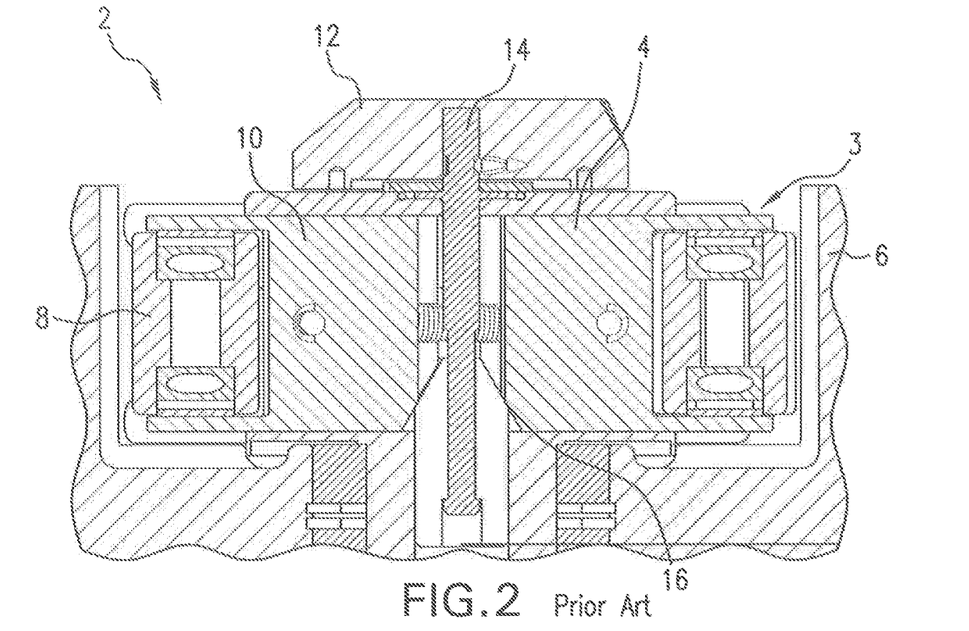
FIG. 2 is a cross-sectional view of a prior art occlusion adjustment mechanism that adjusts roller occlusion in a linear manner.

FIG. 2 illustrates a prior art occlusion adjustment mechanism 2 for a roller pump that is integrated into a pump head 3 of the roller pump, and that moves pump rollers in a linear manner, such as shown by curve A of FIG. 1. The pump head 3 includes a pump rotor 4 disposed to rotate within the pump stator 6. The pump rotor 4 includes a plurality of pump rollers 8 mounted to a corresponding number of roller blocks 10. The occlusion adjustment mechanism 2 includes a knob 12 that may be rotated manually so as to turn an elongated rod 14. A tapered drive piston 16 is threadingly connected to the elongated rod 14 so that rotation of the elongated rod 14 moves the tapered drive piston 16 along the elongated rod 14. Movement of the tapered drive piston 16 on the elongated rod 14 causes the tapered drive piston 16 to push on the plurality of roller blocks 10 so that the tapered drive piston 16 moves the roller blocks 10 in a radial direction with respect to the central axis of the pump head 3 in a linearly and uniform manner. Thus, the knob 12 of this system is connected to screw threads (not specifically illustrated) of the elongated rod 14 in order to advance a wedge (i.e., the tapered drive piston) that drives the rollers 8 towards the housing circumference, namely, the inner circumferential surface of the stator 6, which defines a tubing raceway. For images showing how tubing may be disposed in the raceway of a roller pump, one may consult U.S. Patent Application Publication No. US 2014/0127063 A1, which is incorporated herein by reference in its entirety. A disadvantage associated with the tapered drive piston 16 is that such a wedge is dependent upon precise machining of the wedge sides, and those components that interface with the wedge sides, in order to maintain position symmetry of the rollers 8.

The ratio of input movement, namely knob revolution, to output movement, namely, travel of each roller in a line in the radial direction, as shown graphically in curve A of FIG. 1, constitutes a line for conventional occlusion adjustment mechanisms. This linear relationship may be characterized as movement in a linear manner or as linear transmission. Such movement in a linear manner may be characterized also as movement in a uniform manner since the transmission ratio is constant as well. As a result of such directly proportional movement in a linear manner, a person adjusting the location of the rollers must, turn and turn and turn the knob, or other assembly, when the rollers are located far away from the inner surface of the pump stator. This is a laborious process. On the other hand, when the rollers get close to the inner surface of the pump stator, a person fine tuning the location of the rollers may be frustrated by the fact that the conventional mechanism for adjusting occlusion has no convenient feature for fine tuning when the rollers are in close proximity to the inner surface of the pump stator.

Therefore, there is a need for a mechanism for adjusting occlusion of a roller pump, such as a roller pump employed as a cardiac pump of a heart-lung machine and like devices, that has a non-linear adjustment mechanism, which provides rapid adjusting movement of the pump rollers when the rollers are located at positions farther from the inner surface of the pump stator, and which provides fine adjustment movements of the pump rollers when the rollers are located at positions in close proximity to the inner surface of the pump stator. This disclosure is directed to describing embodiments of apparatuses and methods pertaining to adjustment of occlusion of a roller pump, and like devices, that employ such a non-linear occlusion adjustment mechanism.

SUMMARY OF THE DISCLOSURE

The apparatuses and methods described by this disclosure satisfy the need of users of roller pumps to perform fine adjustment of occlusion, such as is required to meet desired degrees of occlusion for tubing used in a roller pump, such as occurs in the environment of cardiac bypass procedures and like environments. Adjustment of occlusion is effected with greater case through the use of appropriate actuators, such as a manual easy turn knob. Furthermore, the structure of the apparatuses and the nature of the methods described herein allow a manufacturer of roller pumps to make adjustments to the occlusion adjustment mechanism during assembly in order to meet a desired symmetry between rollers. In an embodiment, adjustable drag links provide the ability to make easy adjustments to the symmetry between rollers, although the apparatuses and methods of this disclosure are not limited to the use of adjustable drag links.

The use of adjustable drag links as part of an occlusion adjustment mechanism also has the advantage that it decreases linear travel of rollers progressively with each particular turn of a manual knob, and/or turn of the elongated rod operatively connected to the manual knob. However, the apparatuses and methods of this disclosure are not limited to the use of adjustable drag links to achieve non-linear movement of pump rollers for occlusion adjustment purposes because the operative connection between the manual knob and the non-linear movement of the pump rollers may be effected as an electromechanical connection employing an electronic actuator connected to a motor control device as an alternative to employing a mechanical connection employing adjustable drag links. Thus, in accordance with this disclosure, a quick return mechanism is described as an integral component of the occlusion adjustment mechanism, which effects progressively decreasing increments of linear travel of the pump rollers with each turn of the knob, thereby increasing precision (fine tuning) of each lockable increment of the system as the rollers approach the inner circumferential surface of the pump stator defining the pump raceway.

In accordance with a first, non-limiting illustrative embodiment of this disclosure, a mechanism for adjusting occlusion of a roller pump is described, wherein the mechanism includes: an elongated rod member oriented on a central axis of a pump head of the roller pump; and a drive member attached to the elongated rod member so as to move along the elongated rod member between a first position and a second position, wherein the drive member is connected to each roller block of a pump rotor of the pump head by a link member so that movement of the drive member by constant increments along the elongated rod member causes non-uniform and/or non-linear incremental movement of each roller block in a direction radial to the central axis of the pump head. In accordance with an embodiment of this disclosure, the first non-limiting embodiment may be modified so that the link member comprises a drag link. In accordance with a second, non-limiting embodiment of this disclosure, a roller pump is described, wherein the roller pump includes a pump head operably connected to be driven by a pump drive, wherein the pump head includes: a pump stator comprising an inner circumferential surface defining a raceway; a pump rotor disposed to rotate within the pump stator, wherein the pump rotor includes one or more rollers, wherein each roller is connected to a respective roller block that is moveable radially with respect to a central axis of the pump head; and an occlusion adjustment mechanism connected to the roller block of each roller, wherein the occlusion adjustment mechanism operates to move each roller block radially with respect to the central axis of the pump head in a non-uniform and/or non-linear manner.

In accordance with a third non-limiting illustrative embodiment of this disclosure, the first and second non-limiting embodiments are modified so that the one or more rollers include two rollers disposed on a line bisecting the pump rotor. In accordance with a fourth non-limiting illustrative embodiment of this disclosure, the first, second and third non-limiting embodiments am further modified so that the occlusion adjustment mechanism comprises an elongated rod member oriented on the central axis of the pump head; and a drive member attached to the elongated rod member so as to move along the elongated rod member between a first position and a second position, wherein each roller block is connected by a drag link to the drive member. In accordance with a fifth son-limiting illustrative embodiment of this disclosure, the first, second, third and fourth non-limiting embodiments are further modified so that the drive member is a drive plate or a drive piston.

In accordance with a sixth non-limiting illustrative embodiment of this disclosure, the first, second, third, fourth, and fifth non-limiting embodiments are further modified so that the drive member is threadingly attached to the elongated rod member so that rotation of the elongated rod member causes the drive member to move along the central axis of the pump head between the first position and the second position so that each drag link moves the respective roller block radially with respect to the central ax is of the pump head in the non-uniform manner. In accordance with a seventh non-limiting illustrative embodiment of this disclosure, the first, second, third, fourth, fifth and sixth non-limiting embodiments are modified so that clockwise rotation of the elongated rod member causes the drive member to move up the elongated rod member and causes radial movement of each roller block towards the inner circumferential surface of the pump stator, and counterclockwise rotation of the elongated rod member causes the drive member to move down the elongated rod member and causes radial movement of each roller block away from the inner circumferential surface of the pump stator. In accordance with an eighth non-limiting illustrative embodiment of this disclosure, the first, second, third, fourth, fifth, sixth and seventh non-limiting embodiments are further modified so that each clockwise rotation of the elongated rod member causes a constant incremental movement of the drive member up the elongated rod member and a non-linearly changing incremental movement of each roller block radially towards the inner circumferential surface of the pump stator. In accordance with a ninth non-limiting illustrative embodiment of this disclosure, the first, second, third, fourth, fifth, sixth and seventh non-limiting embodiments am further modified so that the non-linearly changing incremental movement of each roller block is decreasing with each clockwise rotation of the elongated rod.

In accordance with a tenth non-limiting illustrative embodiment of this disclosure, the first, second, third, fourth, fifth and sixth non-limiting embodiments are further modified so that counterclockwise rotation of the elongated rod member causes the drive member to move up the elongated rod member and causes radial movement of each roller block towards the inner circumferential surface of the pump stator, and clockwise rotation of the elongated rod member causes the drive member to move down the elongated rod member and causes radial movement of each roller block away from the inner circumferential surface of the pump stator. In accordance with an eleventh non-limiting illustrative embodiment of this disclosure, the first, second, third, fourth, fifth, sixth and tenth non-limiting embodiments are further modified so that each counterclockwise rotation of the elongated rod member causes a constant incremental movement of the drive member up the elongated rod member and a non-linearly changing incremental movement of each roller block radially towards the inner circumferential surface of the pump stator. In accordance with a twelfth non-limiting illustrative embodiment of this disclosure, the first, second, third, fourth, fifth, sixth, tenth and eleventh non-limiting embodiments are further modified so that the non-linearly changing incremental movement of each roller block is decreasing with each counterclockwise rotation of the elongated rod.

In accordance with a thirteenth non-limiting illustrative embodiment of this disclosure, the first, second, third, fourth, fifth, sixth, seventh, eighth, ninth, tenth, eleventh and twelfth non-limiting embodiments are further modified so that each drag link comprises a ball formed on one end that is connected to a socket formed in the drive member. In accordance with a fourteenth non-limiting illustrative embodiment: of this disclosure, the first, second, third, fourth, fifth, sixth, seventh, eighth, ninth, tenth, eleventh, twelfth and thirteenth non-limiting embodiments are further modified so that each drag link comprises a threaded portion formed on another end that is adjustably connected to a hail member, wherein each ball member is connected to a socket formed in the respective roller block. In accordance with a fifteenth non-limiting illustrative embodiment of this disclosure, the first, second, third, fourth, fifth, sixth, seventh, eighth, ninth, tenth, eleventh, twelfth, thirteenth and fourteenth non-limiting embodiments are further modified so that a knob is connected to one end of the elongated rod member, wherein the knob is configured to be gripped manually and rotated with the elongated rod member.

In accordance with a sixteenth non-limiting illustrative embodiment of this disclosure, the first, second, third, fourth, fifth, sixth, seventh, eighth, ninth, tenth, eleventh, twelfth, thirteenth, fourteenth and fifteenth non-limiting embodiments are further modified so that the drive member is made of a material selected from the group consisting of an oil impregnated metal alloy and a polyether ether ketone resin composition. In accordance with a seventeenth non-limiting illustrative embodiment of this disclosure, the first, second, third, fourth, fifth, sixth, seventh, eighth, ninth, tenth, eleventh, twelfth, thirteenth, fourteenth, fifteenth and sixteenth non-limiting embodiments are further modified so that the drive member comprises a body and a stabilizer attached to the body, wherein the stabilizer prevents the drive member from rotating on the elongated rod member.

In accordance with an eighteenth non-limiting illustrative embodiment of this disclosure, the first, second, third, fourth, fifth, sixth, seventh, eighth, ninth, tenth, eleventh, twelfth, thirteenth, fourteenth, fifteenth and sixteenth non-limiting embodiments are further modified so that each drag link comprises a cam connected by one portion to the drive member and connected by another portion to the respective roller block so that uniform movement of the drive member along the elongated rod member is transmitted and transformed by each drag link to non-uniform movement of the respective roller block. In accordance with a nineteenth non-limiting illustrative embodiment of this disclosure, the first, second and third non-limiting embodiments are further modified so that the occlusion adjustment mechanism comprises an elongated rod member oriented on the central axis of the pump head; a drive member attached to the elongated rod member so as to move along the elongated rod member between a first position and a second position, wherein each roller block is disposed to contact the drive member as the drive member moves from the first position to the second position so that the drive member moves each roller block in a radial direction with respect to the central axis of the pump head; and a motor operably connected to move the drive member attached to the elongated rod member along the elongated rod member, wherein the motor is controlled by an actuator so that movement of the drive member along the elongated rod member is at a first non-uniform rate so that movement of each roller block in the radial direction is at a second non-uniform rate.

DETAILED DESCRIPTION OF EMBODIMENT(S)

Various embodiments in accordance with this disclosure are described with reference to the figures, in which like parts are designated by like reference numbers. The drawings described herein constitute non-limiting illustrations.

As shown in FIGS. 3, 4, 5 and 9, a pump head 20 of a roller pump is operably connected to be driven by a pump drive assembly 22 of the roller pump. The pump head 20 includes a pump stator 24 that is provided with an inner circumferential surface 26 defining a raceway 28 for fluid tubing T (See FIG. 4), and a pump rotor 30 disposed to rotate within the pump stator 24. The pump rotor 30 includes a plurality of rollers 32, most typically two rollers for roller pumps used in cardiopulmonary bypass machines although pump heads having three, six or eight rollers, etc., may also be used. Each roller 32 includes roller bearings 33 to allow it to rotate. The pump rotor 30 includes a plurality of roller blocks 34 so that each roller 32 is connected to a respective roller block 34 that is moveable radially with respect to a central axis 36 of the pump head 20. The pump head 20 also includes an occlusion adjustment mechanism 38 connected to the roller block 34 of each roller 32. The occlusion adjustment mechanism 38 may be construed as an integral component of the pump head 20, and operates to move each roller block 34 radially with respect to the central axis 36 of the pump head in a non-linearly non-uniform manner. A plurality of springs (not shown) with ends attached to each of the roller blocks 34 provide the force that retracts the rollers 32 and insure that the roller blocks 34 maintain forceful contact with drag links 46.

Figure 3:
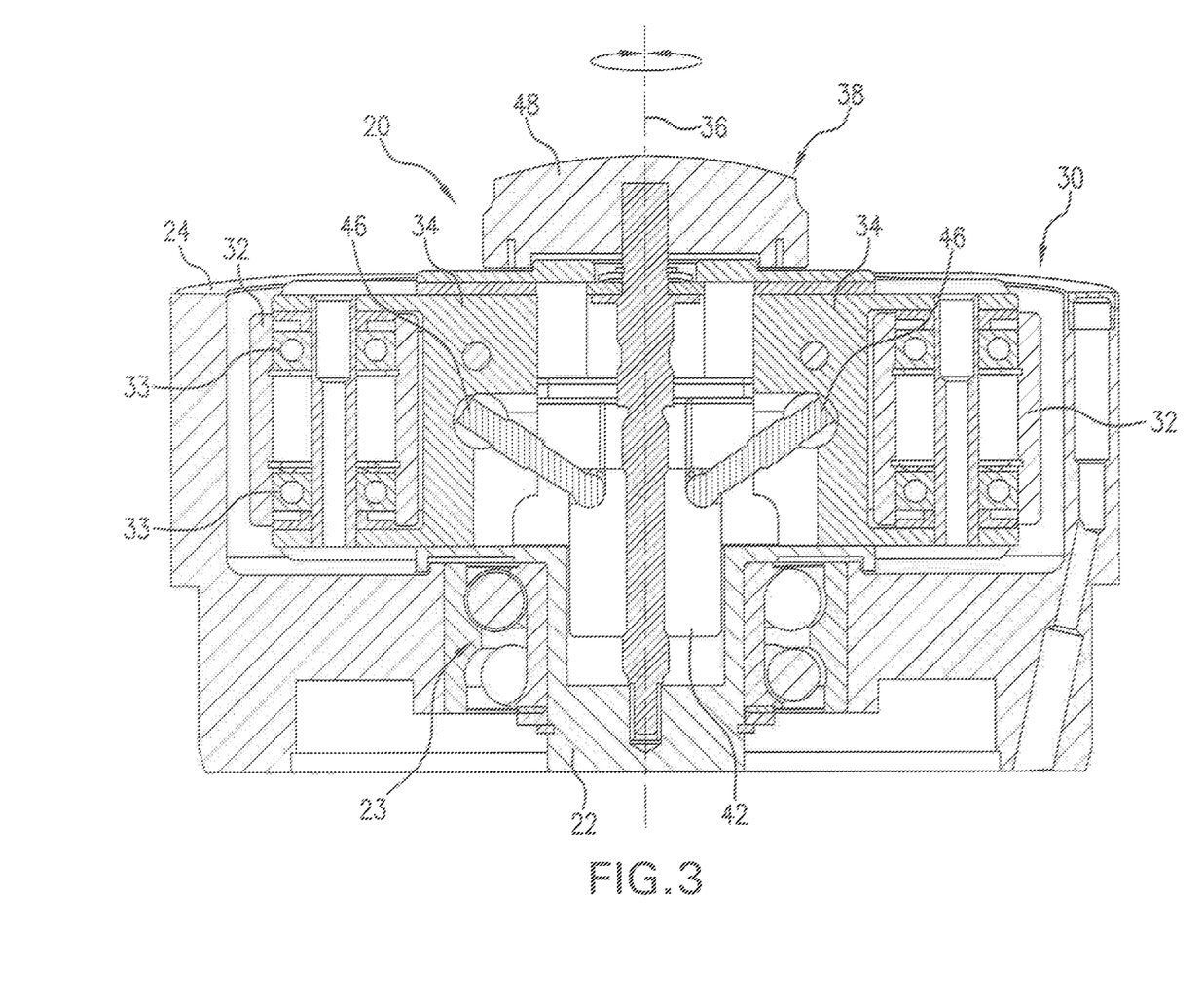
FIG. 3 is a cross-sectional view of an embodiment of a roller pump provided with an occlusion adjustment mechanism as described herein.
Figure 4:
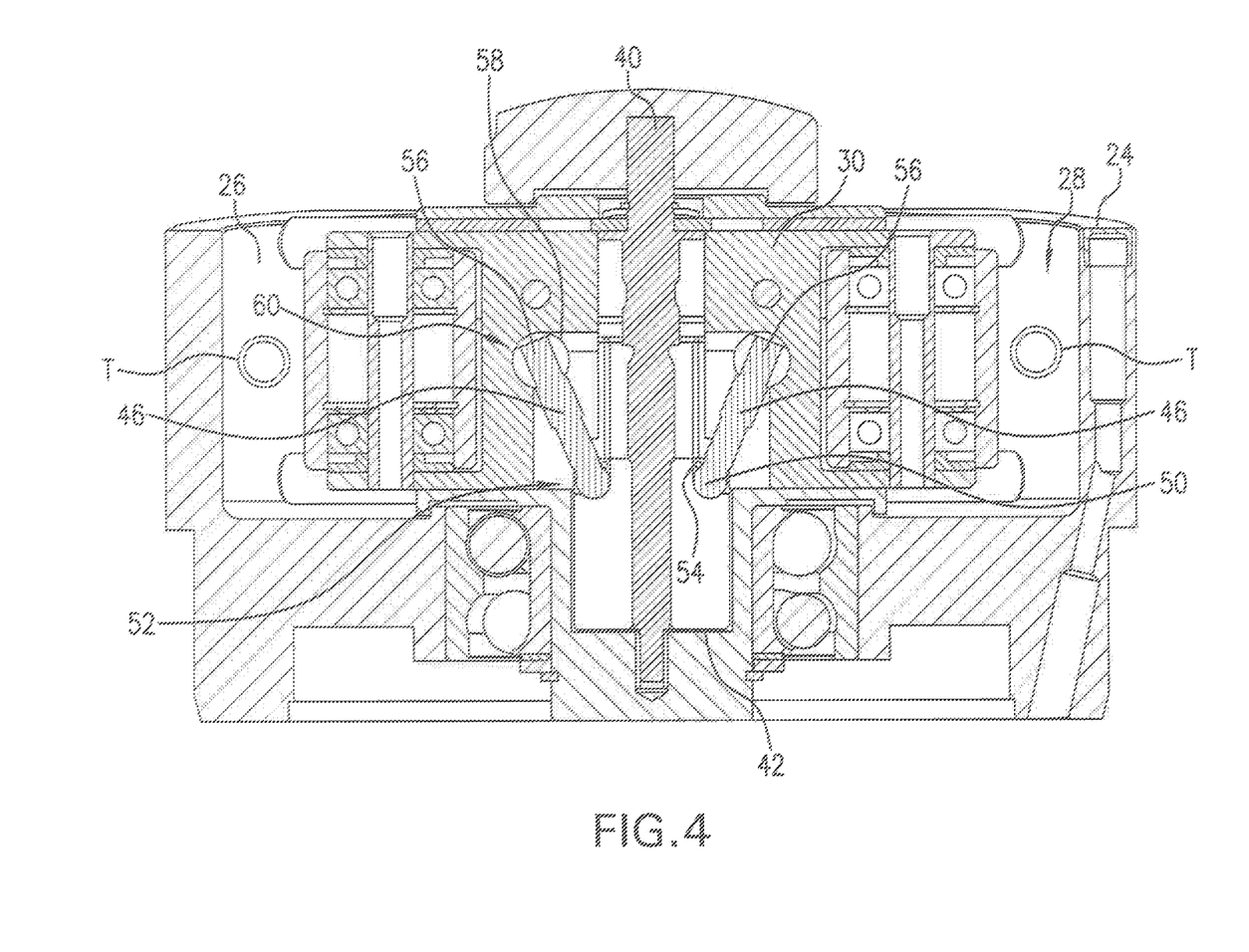
FIG. 4 is a cross-sectional view of the embodiment of FIG. 3 with the roller pumps in a fully retracted state, thereby in a position effecting no occlusion of fluid tubes T.
Figure 5:
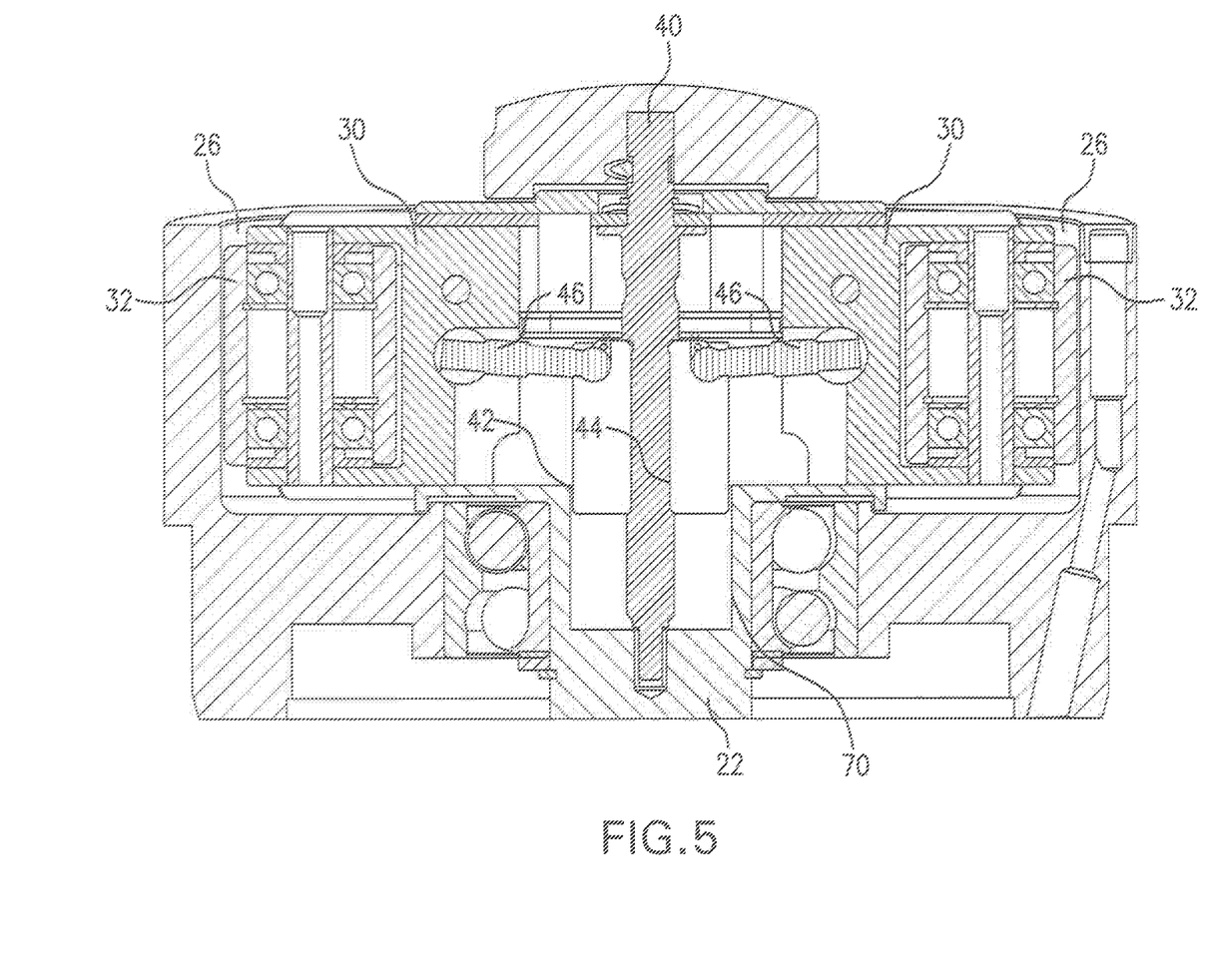
FIG. 5 is a cross-sectional view of the embodiment of FIG. 3 with the roller pumps in a fully extended state, thereby in a position effecting maximum occlusion capacity.

The occlusion adjustment mechanism 38 includes an elongated rod member 40 oriented on the central axis 36 of the pump head 20, and a drive member 42 attached to the elongated rod member 40 so as to move along the elongated rod member between multiple positions. FIG. 3 illustrates the drive member 42 located at an intermediate position on the elongated rod member 40. The range of movement of the drive member 42 on the elongated rod member 40 includes a position at one end of the elongated rod member 40, as shown in FIG. 4, which corresponds to the rollers 32 positioned in a fully retracted position in which the gap of the raceway 28 is maximal, and a position located closer to the other end of the elongated rod member 40, as shown in FIG. 5, which corresponds to the rollers 32 positioned in a fully extended position towards the inner circumferential surface 26 of the stator 24 in which the gap of the raceway 38 is minimal. The drive member 42 is capable of movement between a first position and a second position on the elongated rod member 40 that covers all or part of this range because the elongated rod member 40 is provided with external threads on at least a portion thereof corresponding to the range of movement shown in FIGS. 4 and 5. The drive member 42 includes a central bore 44 formed therethrough, wherein the central bore 44 is provided with internal threads that match and mate with the external threads of the elongated rod member 40, so that the drive member is threadingly connected to the elongated rod member 40 and moves along the elongated rod member 40 when the elongated rod member is rotated. In an embodiment of this disclosure, the elongated rod member 40 is a rotary screw.

The drive member 42 may be a drive plate or a drive piston. A drive plate is a member whose length is less than its diameter. A drive piston is a member whose length is equal to, or greater than, its diameter. In an embodiment of this disclosure, the drive member 42 is made of a self-lubricating material such as an oil impregnated metal alloy (e.g., oil impregnated bronze alloy or oil impregnated iron-based alloy, commercially available and known as Oilite® alloy), or a polyether ether ketone (PEEK) resin composition, such as Ketron® PEEK-HPV, which is a bearing grade PEEK resin composition that includes polytetrafluoroethylene (PTFE), graphite, and carbon fiber. Other materials that may be used to make the drive member 42 include Avalon 75®, which is a PTFE, polyimide-filled thermoplastic polyurethane material, and Torlon® 4301 and Torlon® 4501, which are bearing grade melt processable polyamide-imide plastics, and Ryton® polyphenylene sulfide (PPS), which constitutes bearing grade polyphenylene sulfide that is carbon fiber reinforced and internally lubricated. An advantage to employing self-lubricating materials to construct the drive member 42 is that lubricating materials such as grease maybe omitted. More specifically, many peristaltic pump mechanisms employ grease for lubrication, which is disadvantageous because the grease eventually will become displaced with use. It is also difficult to maintain precision of such a mechanism employing grease because the thickness of the grease constitutes a significant portion of desired tolerance. Thus, the employment of self-lubricating or friction reducing, high wear materials, such as those listed above, is advantageous because the elimination of the need for grease eliminates dimensional changes affecting tolerance caused by grease displacement.

As shown in FIGS. 3, 4 and 5, each roller block 34 is connected by a drag link 46 to the drive member 42. When the drive member 42 moves, which is threadingly attached to the elongated rod member so that rotation of the elongated rod member causes the drive member to move along the central axis of the pump head, then each drag link 46 is caused to move a respective roller block 34 radially with respect to the central axis 36 of the pump head in the non-uniform manner. This is because the drag links 46 are configured to transmit and transform the increments of movement of the drive member 42 in a non-linear, non-uniform manner so that as the drive member 42 moves from its position in FIG. 4 to its position in FIG. 5, an increment of movement by the drive member 42 is transmitted by the drag links 46 to progressively smaller increments of movement of the roller blocks 34. This non-linear, non-uniform movement ratio of input movement (i.e., movement of the drive member 42) to output movement (i.e., movement of roller blocks 34) is graphically represented by curves B, C and D of FIG. 1. Curves B, C and D correspond to different adjustments with respect to the drag links 46 that effect substantial differences in the travel ratio of drive member movement to roller block movement, wherein drive member movement is represented by the number of actuator revolutions (i.e., manual knob revolutions) and roller block movement is represented by millimeters of roller block travel. The "p" values of FIG. 1 pertain to metric thread pitch, which affects the basic rate at which the rollers can advance and retract.

In an embodiment, the threads of the drive member 42 and the elongated rod member 40 are oriented so that clockwise rotation of the elongated rod member causes the drive member to move up the elongated rod member (i.e., to move towards the knob 48), which causes radial movement of each roller block 34 towards the inner circumferential surface 26 of the pump stator 24. Consequently, counterclockwise rotation of the elongated rod member 40 causes the drive member 42 to move down the elongated rod member (i.e., to move away from the knob 48), which causes radial movement of each roller block 34 away from the inner circumferential surface 26 of the pump stator 24 and towards the central axis 36 of the pump head 20. As shown in FIGS. 3, 4 and 5, the elongated rod member 40 is secured to the knob 48 so that when a user grips the knob 48 and manually rotates it, the elongated rod member 40 rotates with the knob 48 to the same degree (i.e., both rotate the same number of turns, or partial turns, and at the same angular velocity, so there is no slippage). Thus, each clockwise rotation of the elongated rod member 40 with the knob 48 causes a constant incremental movement of the drive member 42 up the elongated rod member and, simultaneously, a non-linearly changing incremental movement of each roller block 34 radially towards the inner circumferential surface of the pump stator. In an embodiment, the non-linearly changing incremental movement of each roller block 34 is progressively decreasing with each clockwise rotation of the elongated rod member 40, in a manner as graphically represented by curves B, C and D of FIG. 1.

Curves B, C and D correspond to different metric thread pitches that were evaluated for use in the pumps. These thread pitches, reported as p values, affect the basic rate at which the rollers can advance and retract.

On the other hand, in accordance with an embodiment of this disclosure, it is possible to orient the threads of the elongated rod member 40 and the drive member 42 so that counterclockwise rotation of the elongated rod member 40 causes the drive member 42 to move up the elongated rod member 40 (i.e., towards the knob 48), which causes radial movement of each roller block 34 towards the inner circumferential surface 26 of the pump stator 24, and so that clockwise rotation of the elongated rod member 40 causes the drive member 42 to move down the elongated rod member 40 (i.e., away from the knob 48), which causes radial movement of each roller block 34 away from the inner circumferential surface 26 of the pump stator 24. In other words, it is possible, in accordance with this disclosure, to reverse the thread orientation of the elongated rod member 40 and the drive member 42. In this case, each counterclockwise rotation of the elongated rod member 40 with the knob 48 causes a constant incremental movement of the drive member 42 up the elongated rod member 40 and, simultaneously, a non-linearly changing incremental movement of each roller block 34 radially towards the inner circumferential surface 26 of the pump stator 24. In this embodiment, the non-linearly changing incremental movement of each roller block 34 is progressively decreasing with each counterclockwise rotation of the elongated rod 40, in a manner as graphically represented by curves B, C and D of FIG. 1.

In an embodiment of this disclosure, each drag link 46 may include a ball 50 formed on one end that is connected to a socket 52 formed in the drive member 42 to form a moveable ball joint. This moveable joint may be constructed with a tight running fit between the ball 50 and the socket 52, and a pin 54 may be employed to lock the ball 50 into the socket 52. Furthermore, each drag link 46 may include a threaded portion 56 formed on another end that is adjustably connected to female threads of a ball member 58, and each ball member 58 is connected to a socket 60 formed in the respective roller block 34. Thus, socket 60 and ball member 58 form a moveable ball joint. An advantage of this construction is that adjustment of each drag link 46 with respect to the connection to its roller block 34, provided by the ball joint formed by socket 60 and ball member 58, is possible in view of the adjustable threaded connection between the threaded end 56 of the drag link 46 and the female threads of the ball member 58. Consequently, during assembly, the orientation of each drag link 46 may be fine-timed based on adjustment of the number of turns employed to make the threaded connection between the threaded end 56 and the female threads of the ball member 58.

In an embodiment of this disclosure, a knob 48 is connected to one end of the elongated rod member 40, and the other end of the rod member 40 is connected to a drive shaft of the pump dove assembly 22. The knob 48 is configured to be gripped manually and rotated manually with the elongated rod member 40 so that rotation of the elongated red member 40 actuates movement of the drive member 42 along the elongated rod member 40, which actuates movement of the drag links 46, which transmit the movement of the drive member 42 into radial movement of the roller blocks 34 and the pump rollers 32 mounted to these roller blocks 34. As described above, the configuration of the drag links 46, as connected between the drive member 42 and the roller blocks 34, is responsible for transmitting rotational movement of the knob 48 and elongated rod member 40, which effect a corresponding linear movement of the drive member 42, to a progressively changing movement of the roller blocks 34 in a radial direction. In particular, this progressively changing movement of the roller blocks 34 constitutes, in an embodiment of this disclosure, to a progressively decreasing incremental movement of the roller blocks 34 in the radial direction towards the inner circumferential surface 26 of the stator 24. Consequently, for a fixed rate of rotation of the knob 48 and elongated rod member 40, the rate of movement of the roller blocks 34 and their rollers 32 will progressively decrease as the roller blocks 34 and rollers 32 move from their position in FIG. 4 to their position in FIG. 5.

Figure 6A:
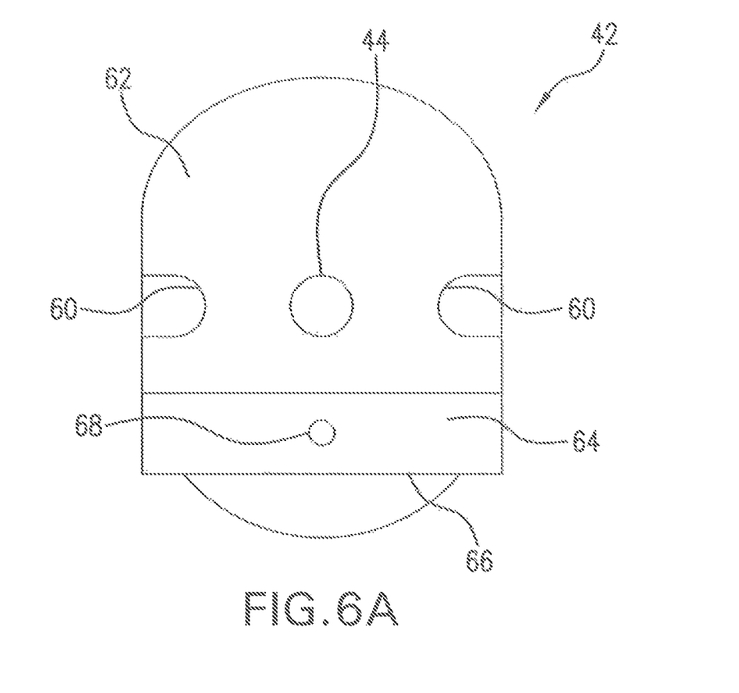
FIG. 6a is a plan view of a drive member in accordance with an embodiment of this disclosure.
Figure 6B:
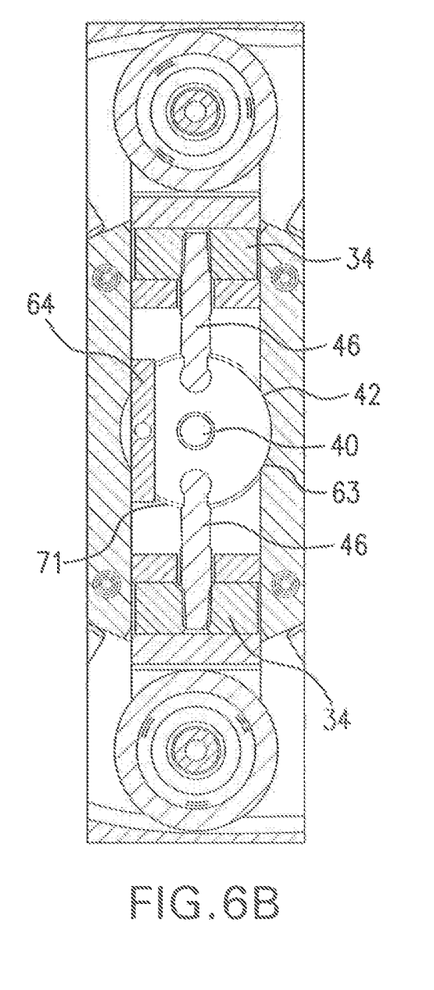
FIG. 6b is a partial plan sectional view of a drive member disposed in a chamber of the drive shaft of the pump drive assembly according to another embodiment of this disclosure.
Figure 6C:
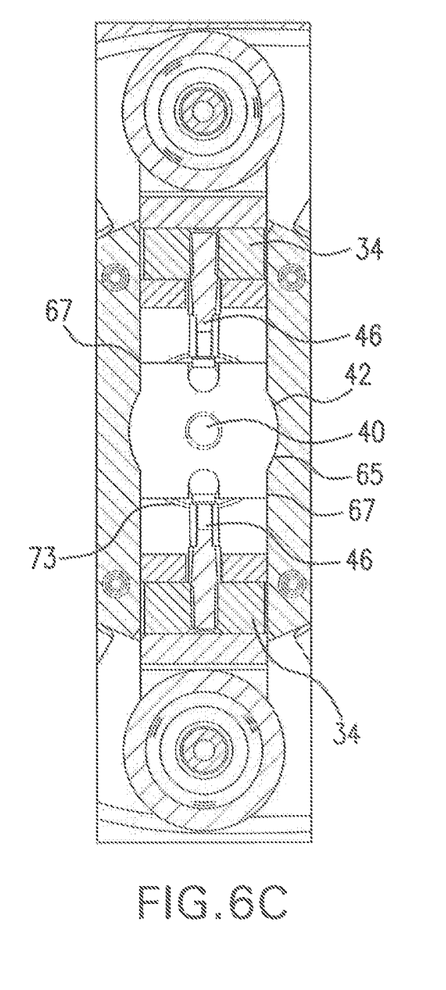
FIG. 6c is a partial plan sectional view of a drive member disposed in a chamber of the draft shall of the pump drive assembly according to another embodiment of this disclosure.

In an embodiment of this disclosure, the drive member 42 includes a body 62 and a stabilizer 64 attached to the body 62, such as shown in FIG. 6a. The stabilizer 64 may constitute a rectangular bar seated in a groove 66 formed in the body 62, wherein the rectangular bar is secured in the groove 66 by a fastener 68, such as a bolt, screw, pin or other suitable device. The groove 66 may have three sides and a U-shaped cross-section, or it may have just two sides and an L-shaped cross-section. The stabilizer 64 prevents the drive member 42 from rotating on the elongated rod member 40. It is desirable that the drive member 42 move efficiently up and down the elongated rod member 40, depending upon the direction of rotation of the elongated rod member 40, so it is important that the drive member 42 does not spin around the elongated rod member 40. In other words, while the elongated rod member 40 is constructed to rotate within the threaded hole of the drive member 42, it is desirable that the elongated rod member 40 does not rotate around the elongated rod member 40. The drive member 42 has a non-circular shape, and is positioned to move in a chamber 70 formed in the drive shaft of the pump drive assembly 22. The pump drive assembly 22 includes one or more bearings 23 that allow the drive shaft to rotate with respect to the pump head 20. The chamber 70 is configured so as to allow translational movement of the drive member 42 along the elongated rod member 40, but the chamber's geometry does not allow the drive member 42 to rotate within the chamber due to interference with the stabilizer 64. In an embodiment of this disclosure, the stabilizer 64, as shown in FIG. 6b, constitutes a separate rectangular bar, which may be made of a substantially different material than the body 63 that is disposed in chamber 71 formed in the drive shaft of the pump drive assembly. On the other hand, in accordance with another embodiment of this disclosure, as shown in FIG. 6c, more than one stabilizer 67 may be integrally formed with the body 65 so these stabilizers 67 are, therefore, made of the same material as the body 65, and prevent rotation of the body 65 of the drive member 42 in the chamber 73 formed in the drive shaft of the pump drive assembly.

Figure 7:
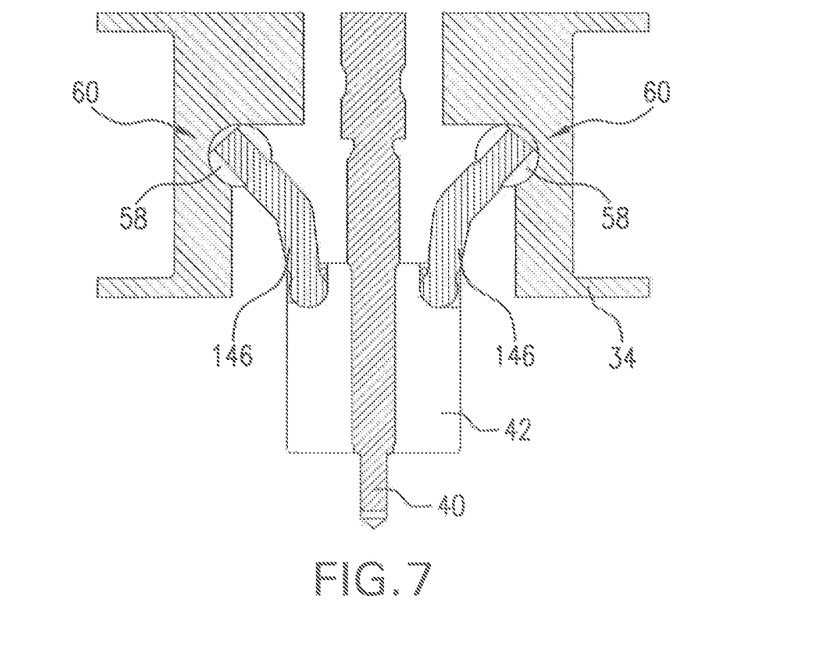
FIG. 7 is a schematic cross-sectional view of a transmission assembly in accordance with an embodiment of this disclosure that employs cams.

In accordance with an embodiment of this disclosure, each drag link is constructed as a cam 146 constructed with geometry as shown in FIG. 7. However, other geometries for the cam 146 may be used to transmit and transform linear movement in constant increments of the drive member 42 along the elongated rod member 40 to radial movement of the roller blocks 34 that is in progressively changing increments, such as shown by curves B, C and D of FIG. 1. For example, each cam 146 may, in accordance with an embodiment of this disclosure, be replaced by an eccentric rotary cam that can be adjusted independent of the position of another eccentric rotary cam positioned on the opposite side of the drive member 42. These eccentric rotary cams are substantially different from the linear wedge 16 of FIG. 2 because the rotary position of each rotary cam may be adjusted independent of the other cam's position on the opposite side of the drive member 42. Thus, eccentric rotary cams provide proportionately non-linear roller displacements in response to translational movement of the drive member, and the eccentric rotary cams permit some adjustment of roller block position during assembly, thereby permitting adjustment with respect to roller occlusion symmetry during initial assembly and calibration of the peristaltic roller pump.

Figure 8:
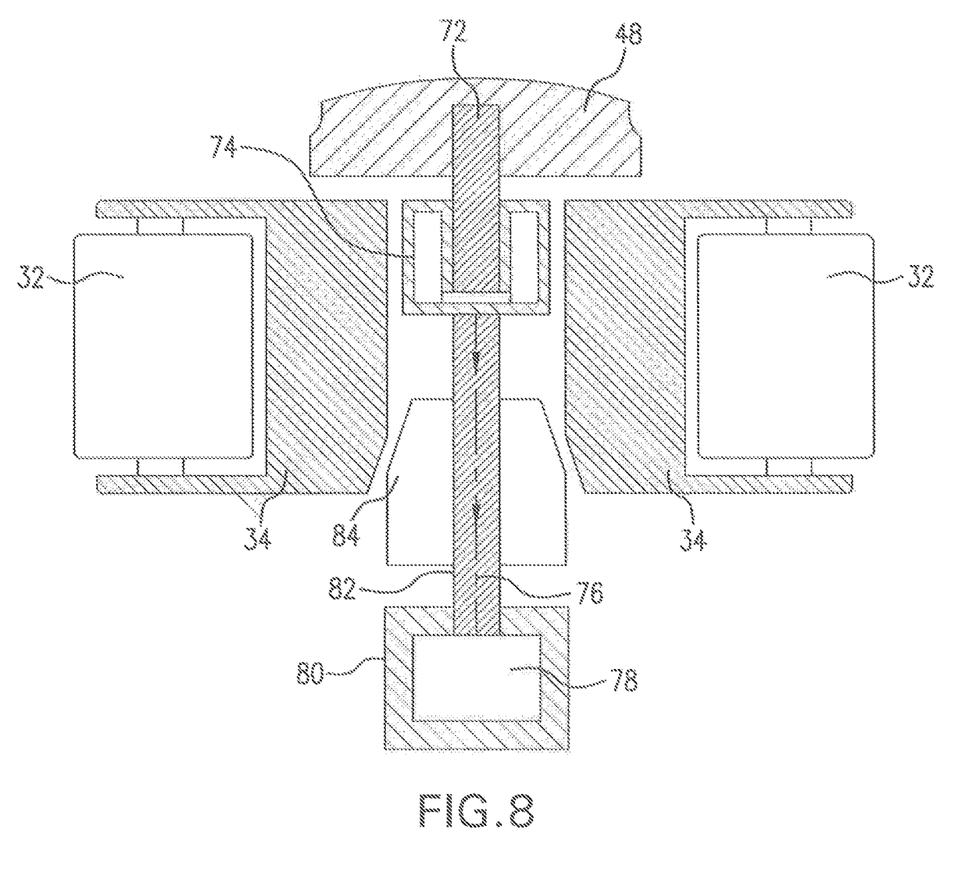
FIG. 8 is a schematic cross-sectional view of an embodiment of an occlusion adjustment mechanism that employs motor control.
Figure 9:
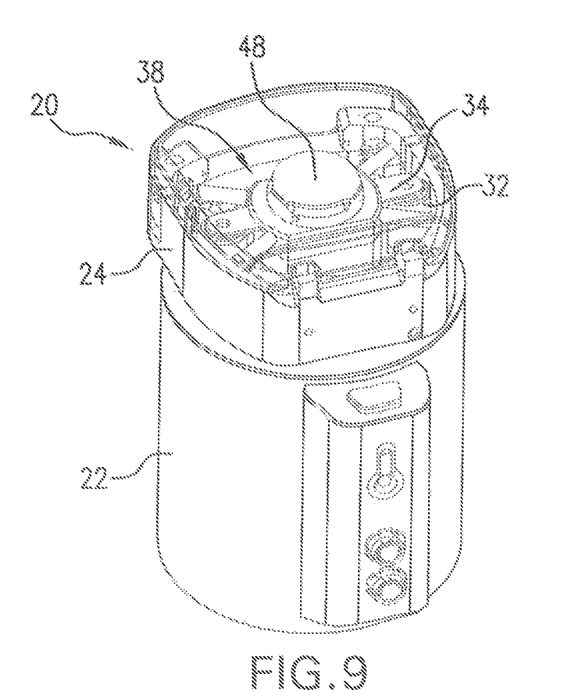
FIG. 9 is a prospective view of a roller pump for a cardiopulmonary bypass machine that employs an occlusion adjustment mechanism in accordance with this disclosure.

In accordance with an embodiment of this disclosure, an occlusion adjustment mechanism may employ motor control of a motor operably connected to rotate the elongated rod member 82 in a non-linear manner that mimics the curves B, C and D of FIG. 1. In such an embodiment, drag links may be omitted. For example, as shown in FIG. 8, the knob 48 is connected to rotate an actuator rod 72, which is operably connected to an actuator 74. The actuator 74 is constructed to sense the position of the actuator rod 72, and is operably connected by an electronic link 76, such as a wire or wireless connection, to the motor control 78 of a motor 80. The motor 80 is operably connected to rotate the elongated rod member 82, which is not connected by any physical link to rotate with the knob 48 and/or the actuator rod 72. On site contrary, the "link" between rotation of actuator rod 72 and rotation of elongated rod member 82 is an electromechanical coupling in which signals generated by the actuator 74 are received by the motor control 78, which uses the signals to generate motor control signals that control operation of the motor 80. The elongated rod member 82 is provided with an external thread, which engages with the internal thread (female thread) of the drive member 84, so that the drive member 84 moves up and down along the elongated rod member 82 in a manner similar to how the drive member 42 moves up and down the elongated rod member 40. Movement of the drive member 84 on the elongated rod member 82 causes the roller blocks 34 and their rollers 32 to move in the radial direction in a manner similar to the transmission assembly of the occlusion adjustment mechanism 2 of FIG. 2 because drive member 84 is a tapered drive piston. Consequently, the rotation of the elongated rod member 82 causes movement of the drive member 84 up and down the elongated rod member 82 in a manner that couples roller displacement to rod revolutions in a manner similar to curve A of FIG. 1. However, through appropriate motor control, the revolutions of knob 48 can be transmitted to non-uniform roller displacement in a manner that mimics the non-linear transmission according to curves B, C and D of FIG. 1.

In other words, in accordance with the embodiment illustrated in FIG. 8, the motor 80 is operably connected to move the drive member 84 attached to the elongated rod member 82 along the elongated rod member 82, wherein the motor 80 is controlled by the actuator 74, which generates signals based on knob 48 movement that are used by the motor controller 78 to control rotation of the rotation rate of the elongated rod member 82. In this way, movement of the drive member 84 along the elongated rod member 82 may be controlled at a first non-uniform rate so that movement of each roller block 34 in the radial direction is controlled at a second non-uniform rate. For example, when the roller blocks 34 are located closer so their fully retracted position, the motor controller 78 controls the motor 80 to rotate the elongated rod member 82 at a faster rate than when the roller blocks 34 are located at a position that is closer to the inner circumferential surface 26 of the stator 24. As a result, the drive member 84 moves up the elongated rod member 82 at a faster rate when the roller blocks 34 are further away from the inner circumferential surface 26 of the stator 24 than when the roller blocks 34 are closer to the inner circumferential surface 26. Consequently, the rate at which the roller blocks 34 move radially towards the inner circumferential surface 26 slows down progressively, due to appropriately programmed motor control, to mimic the relationship between roller displacement versus knob 48 rotation affected by a mechanical transmission assembly utilizing drag links, such as is represented by curves B, C and D of FIG. 1.

In accordance with a method embodiment of this disclosure, a method of adjusting occlusion of a roller pump may include the steps of: (a) disposing a compressible fluid conduit in a raceway of a roller pump head, wherein the raceway is defined by an inner circumferential surface of a stator of the roller pump head, and the fluid conduit includes a lumen through which fluid flows; and (b) operating an occlusion adjustment mechanism of the roller pump head so as to move a plurality of roller blocks of the roller pump head in a radial direction with respect to a central axis of the pump head so as to partially occlude the lumen of the compressible fluid conduit by compressing the compressible fluid conduit between a plurality of rollers mounted on the plurality of roller blocks, wherein the occlusion adjustment mechanism moves the plurality of roller blocks towards the inner circumferential surface of the stator in a non-linear and/or non-uniform manner, such as shown by curves B, C and D of FIG. 1. This method may be further modified so that movement of the plurality of roller blocks towards the inner circumferential surface of the stator in the non-uniform manner comprises moving a drive member along an elongated rod member, wherein the moving drive member causes radial movement of the plurality of roller blocks in decreasing increments as the plurality of roller blocks move closer to the inner circumferential surface of the stator of the roller pump head. As described above, this movement of the plurality of roller blocks in decreasing increments may be effected by using a transmission assembly according to FIG. 3, which employs drag links, or by using a transmission assembly according to FIG. 8 with appropriate motor control to mimic the movement of the roller blocks 34 achieved by the transmission assembly according to FIG. 3.

Notably, because of the occlusion adjusting mechanisms described above, specifically because of the geometry of those mechanisms in which the movement of the links 46 is in response to the verticality moving drive member 42, radially outward and inward movements of the rollers 32 are proportionally non-linear relative to the amount of knob 48 rotation. This is a desirable feature because it allows for finer adjustments of the roller positions in the range of movement required to cause tubing partial occlusion, thus setting flow rates. As described above, this desirable feature may be achieved using an occlusion adjusting mechanism as shown in FIG. 8 that employs appropriate control of a motor 80. In embodiments of the occlusion adjusting mechanism employing the links 46, in which each link 46 is composed of a bar and a ball 50 that allows the link 46 to be adjustable, alternative structures for the links 46 may be used. For example, each link 46 may be composed of several parts that allow the link to be length-adjustable, such as by having additional portions of the link thread into other portions of the link. Having a length-adjustable link is highly desirable because it facilitates the initial setting of roller position symmetry, which facilitates the initial setting of occlusion symmetry, during the manufacturing process.

In accordance with an embodiment of this disclosure, a dual-link configuration may be employed. In this embodiment, each link is constructed with two adjacent links on each side. Thus, each link is constructed as a set of two adjacent links forming a triangle, with the apex of the triangle connected to the roller blocks 34, and the base of the triangle is connected to the drive member. As the drive member moves vertically up and down the elongated rod member 40, the height of the triangle changes thereby changing the position of the roller blocks 34. This dual-link configuration may be embodied as a classic centrifugal governor linkage.

While apparatuses and methods have been described with reference to certain embodiments within this disclosure, one of ordinary skill in the art will recognize, that additions, deletions, substitutions and improvements can be made while remaining within the scope and spirit of the invention as defined by the appended claims.

What is claimed is:

1. A roller pump comprising a pump head operably connected to be driven by a pump drive, wherein the pump head includes:
   a pump stator comprising an inner circumferential surface, defining a raceway;
   a pump rotor disposed to rotate within the pump stator, wherein the pump rotor includes
      one or more rollers, wherein each roller is connected to a respective roller block that is moveable radially with respect to a central axis of the pump head; and
   an occlusion adjustment mechanism, connected to the roller block of each roller, wherein the occlusion adjustment mechanism operates to move each roller block radially with respect to the central axis of the pump head in a non-uniform manner.

2. The roller pump of claim 1, wherein the one or more rollers include two rollers disposed on a line bisecting the pump rotor.

3. The roller pump of claim 1, wherein the occlusion adjustment mechanism comprises
   an elongated rod member oriented on the central axis of the pump head; and
   a drive member attached to the elongated rod member so as to move along the elongated rod member between a first position and a second position, wherein each roller block is connected by a drag link to the drive member.

4. The roller pump of claim 3, wherein the drive member is a drive plate or a drive piston.

5. The roller pump of claim 3, wherein the drive member is threadingly attached to the elongated rod member so that rotation of the elongated rod member causes the drive member to move along the central axis of the pump head between the first position and the second position so that each drag link moves the respective roller block radially with respect to the central axis of the pump head in the non-uniform manner.

6. The roller pump of claim 5, wherein clock wise rotation of the elongated rod member causes the drive member to move rip the elongated rod member and causes radial movement of each roller block towards the inner circumferential surface of the pump stator, and counterclockwise rotation of the elongated rod member causes the drive member to move down the elongated rod member and causes radial movement of each roller block away from the inner circumferential surface of the pump stator.

7. The roller pump of claim 6, wherein each clockwise rotation of the elongated rod member causes a constant incremental movement of the drive member up the elongated rod member and a non-linearly changing incremental movement of each roller block radially towards the inner circumferential surface of the primp stator.

8. The roller pump of claim 7, wherein the non-linearly changing incremental movement of each roller block is decreasing with each clockwise rotation of the elongated rod.

9. The roller pump of claim 5, wherein counterclockwise rotation of the elongated rod member causes the drive member to move up the elongated rod member and causes radial movement of each roller block towards the inner circumferential surface of the pump stator, and clockwise rotation of the elongated rod member causes the drive member to move down the elongated rod member and causes radial movement of each roller block away from the inner circumferential surface of the pump stator.

10. The roller pump of claim 9, wherein each counterclockwise rotation of the elongated rod member causes a constant incremental movement of the drive member up the elongated rod member and a non-linearly changing incremental movement of each roller block radially towards the inner circumferential surface of the pump stator.

11. The roller pump of claim 10, wherein the non-linearly changing incremental movement of each roller block is decreasing with each counterclockwise rotation of the elongated rod.

12. The roller pump of claim 3, wherein each drag link comprises a ball formed on one end that is connected to a socket formed in the drive member.

13. The roller pump of claim 12, wherein each drag link comprises a threaded portion formed on another end that is adjustably connected to a ball member, wherein each ball member is connected to a socket formed in the respective roller block.

14. The roller pump of claim 3, wherein a knob is connected to one end of the elongated rod member, wherein the knob is configured to be gripped manually and rotated with the elongated rod member.

15. The roller pomp of claim 3, wherein the drive member is made of a material selected from the group consisting of an oil impregnated metal alloy and a polyether ether ketone resin composition.

16. The roller pump of claim 3, wherein the drive member comprises a body and a stabilizer attached to the body, wherein the stabilizer prevents the drive member from rotating on the elongated rod member.

17. The roller pump of claim 3, wherein each drag link comprises a cam connected by one portion to the drive member and connected by another portion to the respective rosier block so that uniform movement of the drive member along the elongated rod member is transmitted and transformed by each drag link to non-uniform movement of the respective roller block.

18. The roller pump of claim 1, wherein the occlusion adjustment mechanism comprises
an elongated rod member oriented on the central axis of the pump head;
a drive member attached to the elongated rod member so as to move along the elongated rod member between a first position and a second position, wherein each roller block is disposed to contact the drive member as the drive member moves from the first position to the second position so that the drive member moves each roller block in a radial direction with respect to the central axis of the pump head; and
a motor operably connected to move the drive member attached to the elongated rod member along the elongated rod member, wherein the motor is controlled by an actuator so that movement of the drive member along the elongated rod member is at a first non-uniform rate so that movement of each roller block in the radial direction is at a second non-uniform rate.

19. A mechanism for adjusting occlusion of a roller pump, wherein the mechanism comprises:
an elongated rod member oriented on a central axis of a pump head of the roller pump; and
a drive member attached to the elongated rod member so as to move along the elongated rod member between a first position and a second position, wherein the drive member is connected to each roller block of a pump rotor of the pump head by a link member so that movement of the drive member by constant increments along the elongated rod member causes non-uniform incremental movement of each roller block in a direction radial to the central axis of the pump head.

20. The mechanism according to claim 19, wherein the link member comprises a drag link.

21. A method of adjusting occlusion of a roller pump, the method comprising the steps of:
disposing a compressible fluid conduit in a raceway of a roller pump head, wherein the raceway is defined by art inner circumferential surface of a stator of the roller pump head, and the fluid conduit includes a lumen through which fluid flows; and
operating an occlusion adjustment mechanism of the roller pump head so as to move a plurality of roller blocks of the roller pump head in a radial direction with respect to a central axis of the pump head so as so partially occlude the lumen of the compressible fluid conduit by compressing the compressible fluid conduit between a plurality of rollers mounted on the plurality of roller blocks, wherein the occlusion adjustment mechanism moves the plurality of roller blocks towards the inner circumferential surface of the stator in a non-uniform manner.

22. The method of claim 21, wherein movement of the plurality of roller blocks towards the inner circumferential surface of the stator in the non-uniform manner comprises moving a drive member along an elongated rod member, wherein the moving drive member causes radial movement of the plurality of roller blocks in decreasing increments as the plurality of roller blocks move closer to the inner circumferential surface of the stator of the roller pump head.

* * * * *

UNITED STATES PATENT AND TRADEMARK OFFICE
CERTIFICATE OF CORRECTION

PATENT NO. : 10,583,233 B2  
APPLICATION NO. : 15/571010  
DATED : March 10, 2020  
INVENTOR(S) : William James Repka et al.

Page 1 of 1

It is certified that error appears in the above-identified patent and that said Letters Patent is hereby corrected as shown below:

In the Claims

Column 14, Line 55, Claim 6, delete "rip" and insert -- up --

Column 16, Line 33, Claim 21, delete "art" and insert -- an --

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*